United States Patent [19]

Alpins

[11] Patent Number: 6,086,579
[45] Date of Patent: *Jul. 11, 2000

[54] METHOD OF ANALYZING ASTIGMATISM AND APPARATUS FOR PERFORMING CORNEAL SURGERY

[76] Inventor: Noel Ami Alpins, 7 Chesterville Road, Cheltenham, Vic. 3192, Australia

[*] Notice: This patent is subject to a terminal disclaimer.

[21] Appl. No.: 09/075,675

[22] Filed: May 11, 1998

Related U.S. Application Data

[62] Continuation of application No. 08/618,535, Mar. 19, 1996, Pat. No. 5,749,867, which is a division of application No. 08/313,056, filed as application No. PCT/AU93/00090, Mar. 4, 1993, Pat. No. 5,514,124, which is a continuation-in-part of application No. 07/927,616, Aug. 10, 1992, abandoned.

[51] Int. Cl.$^7$ .......................................... A61N 5/06
[52] U.S. Cl. ................................... 606/4; 606/5; 128/898
[58] Field of Search ................................ 606/4, 1, 6, 10, 606/11, 12; 128/898

[56] References Cited

U.S. PATENT DOCUMENTS

| | | |
|---|---|---|
| 3,880,502 | 4/1975 | Humphrey . |
| 3,947,097 | 3/1976 | Humphrey . |
| 4,718,418 | 1/1988 | L'Esperance, Jr. . |
| 4,721,379 | 1/1988 | L'Esperance . |
| 5,102,409 | 4/1992 | Belgorod . |
| 5,190,057 | 3/1993 | Sartarazi . |
| 5,423,801 | 6/1995 | Marshall et al. . |
| 5,556,395 | 9/1996 | Shimmick et al. . |

FOREIGN PATENT DOCUMENTS

| | | |
|---|---|---|
| 247260 | 12/1987 | European Pat. Off. . |
| 257836 | 3/1988 | European Pat. Off. . |
| 296982 | 12/1988 | European Pat. Off. . |
| 2581307 | 11/1986 | France . |
| 9116023 | 10/1991 | WIPO . |

OTHER PUBLICATIONS

Cravy, T.V. "Calculation of the Charge.." Opthalmic Surgery, vol. 10, No. 1, Jan. 1979, pp. 38–49.

Jaffe, N.S. et al. "The Pathophysiology of Corneal Astigmatism.." Trans Am Acad. Opthaalmol Otolaryngol, vol. 79, 1975 pp. 615–630.

*Primary Examiner*—Michael Peffley
*Attorney, Agent, or Firm*—Ladas & Parry

[57] ABSTRACT

A method of analyzing astigmatism is disclosed which enables surgeons to ascertain what surgery may be required subsequent to initial surgery to achieve the preoperative aim of the initial surgery. The method includes determining a preoperative astigmatism, defining an aimed astigmatism and determining an achieved astigmatism following initial surgery. The astigmatism values are initially determined in a zero to 180 degree range and are doubled to convert them to a 360 degree range. An aimed induced astigmatism vector and a surgically induced astigmatism vector are calculated by vectorially adding the preoperative astigmatism respectively to the aimed astigmatism and the post-operative astigmatism. Magnitudes and angles of the vectors are related to one another and to their component values for providing fundamental information regarding the past surgery, improved performance of possible future surgery and also what alteration to the first surgical plan would have been required to have achieved the initial aimed astigmatism. The method also provides a rationale for determining treatment parameters when spectacle and corneal astigmatism do not coincide.

28 Claims, 4 Drawing Sheets

METHOD OF ANALYZING ASTIGMATISM AND APPARATUS FOR PERFORMING CORNEAL SURGERY

This application is a continuation of application 08/618,535 filed Mar. 19, 1996 now U.S. Pat. No. 5,749,867, which is a division of Ser. No. 08/313,056 filed Sep. 30, 1994, now U.S. Pat. No. 5,514,124, which is National Stage Entry of International Application PCT/AU93/00090 filed on Mar. 4, 1993 and which designated the U.S., which is a continuation-in-part of Ser. No. 07/927,616 filed Aug. 10, 1992 now abandoned.

This invention relates to a method of analysing astigmatism which can be used to provide information to enable surgeons to correct astigmatism in patients and also to provide data relating to surgical operations for correcting astigmatism which surgeons can use to improve techniques and surgical success, and also to an apparatus for performing corneal surgery.

Current methods of analysing astigmatism are confined to calculation of the vector of change surgically induced in attaining the post-operative result from the pre-operative state.

This ably allows determination of total induced astigmatism and the direction of the vector force acting in the eye. It also enables calculation of the mean total surgical astigmatism induced when a series of operations are compared and analysed. However, the axes of surgically induced astigmatism (SIA) generally varies considerably within the 180° arc of range. This makes it extremely difficult to make meaningful comparisons of astigmatic change for a series, as one cannot obtain an average directional change of vectors, as vectors in opposing or partly opposing directions cancel each other out in varying amounts.

One practice carried out by some surgeons is to resort to the sole option of tabulating each patient's results individually, leaving it to the reader to estimate any trend. Some surgeons attempt to provide an overview of results, but lack the means to deduce a trend in induced astigmatism vectors as a group, because they have variable orientation.

Taking a mean of the angles has no validity in determining the trend for axes, nor does it address the change in axes from their pre-operative to post-operative astigmatic status. It does not assess the success or desirability of the achieved result; furthermore, it does not indicate the extent to which the surgical aim was achieved. An attempt has been made to address the complexities of correcting the magnitude for the degrees of axis change by introducing the approximation that this component varies as the cosine of the difference between the attempted and the observed (achieved) axes. This corrected value of magnitude was substituted as the amount of surgically induced cylinder 90° to the axis of the incisions, the so-called "proper" axis. It has been proposed to program so called Naylor's equations into a computer program that requires slight modifications to resolve the ambiguity and essentially reproduce the Naylor table.

The formula for calculation of SIA is derived from the resultant of two plano-cylindrical lenses with axes at different angles; this was subsequently employed by some surgeons using graphical method confirming the magnitude and axis of the astigmatic change. Jaffe and Clayman employ rectangular and polar co-ordinates to determine, by vector analysis, the formula for calculating SIA and its axis with the known values for pre- and post-operative corneal astigmatism. Analogous formulae were derived by Hall based on Martin and Welford's derivation of Euler's theorem of curved surfaces (investigated by Airy in 1827). Euler's theorem, which states "that the sum of the curvatures of any two perpendicular sections of a cylindrical or toric surface has a constant value", provides the link between Jaffe's and Naeser's methods of vector analysis. Naeser's method calculates the polar values of astigmatism, arising when the axis of astigmatism does not lie on 90° or 180° meridia; its use lies primarily in interpreting results of surgery which induces polar (with-the-rule and against-the-rule) changes, such as cataract and implant surgery (with or without transverse astigmatic keratotomy).

Astigmatism is a unique refractive error that causes reduced visual acuity and produces symptoms such as glare, monocular diplopia, asthenopia and distortion. For some years now, astigmatism control and correction has been of great concern to refractive, cataract and corneal surgeons. Reduction or elimination of astigmatism, as a single or combined procedure, is only possible if one possesses an understanding of astigmatic change, in its component parts of magnitude and axis. Current analytical techniques do not allow us to compare magnitudes and axes separately for a series of paired groups of procedures or for a single procedure, yet it is only in this way that we are able to perfect techniques of astigmatism surgery. We need to be able to determine the preferable technique to employ; we also need to be able to determine whether any failure to achieve surgical goals is attributable to an individual patient factor or to machine or technique error. Modern laser technologies have empowered us with the ability to modify our procedures with degrees of sophistication not previously possible; this in turn requires analysis systems which will allow us to accurately quantify and scientifically assess the results.

The object of the present invention is to provide a method which allows more meaningful information to be obtained which can be used by surgeons to provide a greater degree of success when applied to an individual patient and also to provide statistical information which will enable techniques to be improved.

The present invention provides a method of analysing astigmatism comprising the steps of:
  determining a pre-operative astigmatism;
  defining an aimed astigmatism;
  calculating an aimed induced astigmatism vector which is the difference between the aimed astigmatism and the pre-operative astigmatism; and
  calculating from the aimed induced astigmatism vector the direction and amount of relative steepening of the cornea to provide orientation of a surgical procedure in magnitude and direction.

The aimed induced astigmatism vector may be modified by an angle of error and a magnitude of error.

The present invention also provides a method of analysing astigmatism comprising the steps of:
  determining a pre-operative astigmatism;
  defining an aimed astigmatism;
  determining an achieved astigmatism following a surgical procedure;
  calculating an aimed induced astigmatism vector which is the difference between the aimed astigmatism and the pre-operative astigmatism, calculating a surgically induced astigmatism vector which is the difference between the achieved astigmatism and the pre-operative astigmatism and calculating a difference vector which is the difference between the aimed astigmatism and the achieved astigmatism to enable magnitudes of the vectors and angles of the vectors to be obtained.

The present invention also provides a method of analysing astigmatism comprising the steps of:

determining a pre-operative astigmatism including a magnitude and axis of astigmatism in a 0° to 180° range;

defining an aimed astigmatism including a magnitude and axis, the axis being an angle presented in a 0° to 180° range;

determining an achieved astigmatism following a surgical procedure, the achieved astigmatism having a magnitude an axis, the axis being an angle presented in a 0° to 180° range;

doubling the angles of the axes of the pre-operative astigmatism, aimed astigmatism and achieved astigmatism to convert the axes to a 360° range;

calculating an aimed induced astigmatism vector which is the difference between the aimed astigmatism and the pre-operative astigmatism calculating a surgically induced astigmatism vector which is the difference between the achieved astigmatism and the pre-operative astigmatism, and calculating a difference vector which is the difference between the aimed astigmatism and the achieved astigmatism; and halving the angle of the aimed induced astigmatism vector, the surgically induced astigmatism vector and the difference vector to return the angle values to a 0° to 180° range and calculating the magnitudes of the vectors to thereby provide astigmatism vector magnitude values and vector angle values.

Since the method produces astigmatism magnitude values and angle values, and in particular an aimed induced astigmatism vector and a difference value, results obtained can be used to predict trends in surgery to enable techniques to be improved and also to use particular results for a particular patient in order to surgically correct a previously surgically induced astigmatism to an aimed induced astigmatism.

Preferably the step of doubling the vector angles includes the step of converting from polar coordinates to rectangular coordinates.

Preferably the step of determining pre-operative astigmatism comprises making corneal measurements of a patient or, in an alternative embodiment, utilising information relating to glasses prescription of the patient.

Preferably the method includes a step of determining a coefficient of adjustment by dividing the aimed induced astigmatism vector by the surgically induced astigmatism vector.

Preferably the method includes determining an angle or error and a magnitude of error which are respectively the angle difference and magnitude difference between the surgically induced astigmatism vector and the aimed induced astigmatism vector.

Preferably the method includes determining an index of success which is the magnitude of the difference vector divided by the magnitude of the aimed induced astigmatism vector.

Preferably the method includes determining an angle of correction which is the angular difference between aimed astigmatism and the achieved astigmatism.

Preferably the method includes calculating an angle of error which is the angular difference between of the surgically induced astigmatism vector and the aimed induced astigmatism vector.

Preferably the method includes a step of determining an angle of the difference vector and the magnitude of the difference vector.

The present invention may also be said to reside in an apparatus for performing corneal surgery comprising:

means for performing surgery on a patient's cornea;

control means for controlling the means for performing surgery; and processing means for receiving an aimed induced astigmatism vector which is the difference between aimed astigmatism and pre-operative astigmatism of the patient and for outputting signals to control the control means in accordance with the aimed induced astigmatism vector.

Preferably the means for performing surgery comprises a source of ultraviolet radiation and a shutter device and the control means controls the opening duration of the shutter device and the intensity of the source of ultraviolet radiation.

Preferably the processing means includes input means for inputting data relating to pre-operative astigmatism of the patient and aimed astigmatism so that the processing means can calculate the aimed induced astigmatism vector.

A preferred embodiment of the invention will be described, by way of example, with reference to the accompanying drawings in which.

Figure 1:
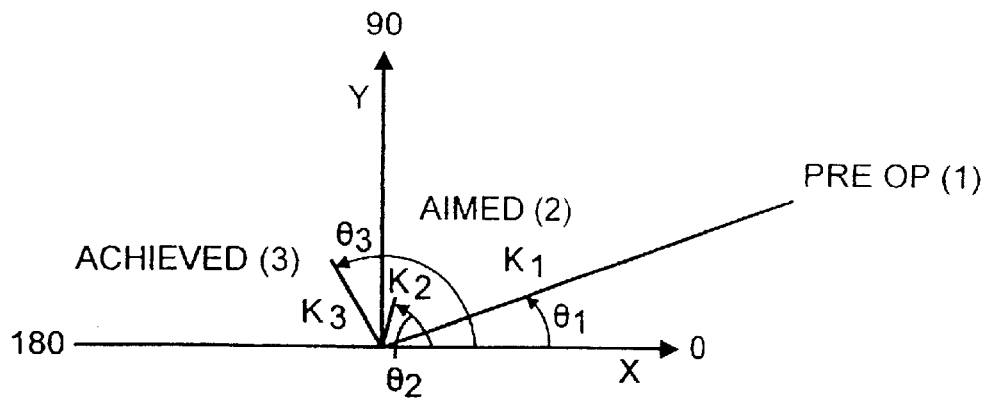
FIG. 1 is a graph showing typical pre-operative, aimed and achieved astigmatisms for a patient.

The astigmatism values used to assess results are shown in FIG. 1 for a typical patient and are:

(1) Pre-operative astigmatism, magnitude $K_1$ diopters at steepest axis $\theta_1$ (2) Aimed astigmatism, magnitude $K_2$ diopters at steepest axis $\theta_2$ (3) Achieved astigmatism, magnitude $K_3$ diopters at steepest axis $\theta_3$ where $K_1$, $K_2$, and $K_3$ are the dioptric differences between the steepest and flattest curvatures of the cornea, at the steepest axes $\theta_1$, $\theta_2$ and $\theta_3$ For example the pre-operative astigmatism is 4.00 diopters at 20°.

Astigmatism is normally represented in a 0° to 180° sense. This representation complicates interpretation of results in that a change in astigmatism from, say, a pre-operative value of 5° to a post-operative value of 175° appears both visually, on a graph, and numerically to be a 170° change whereas it is in fact only a 10° change.

Figure 2:
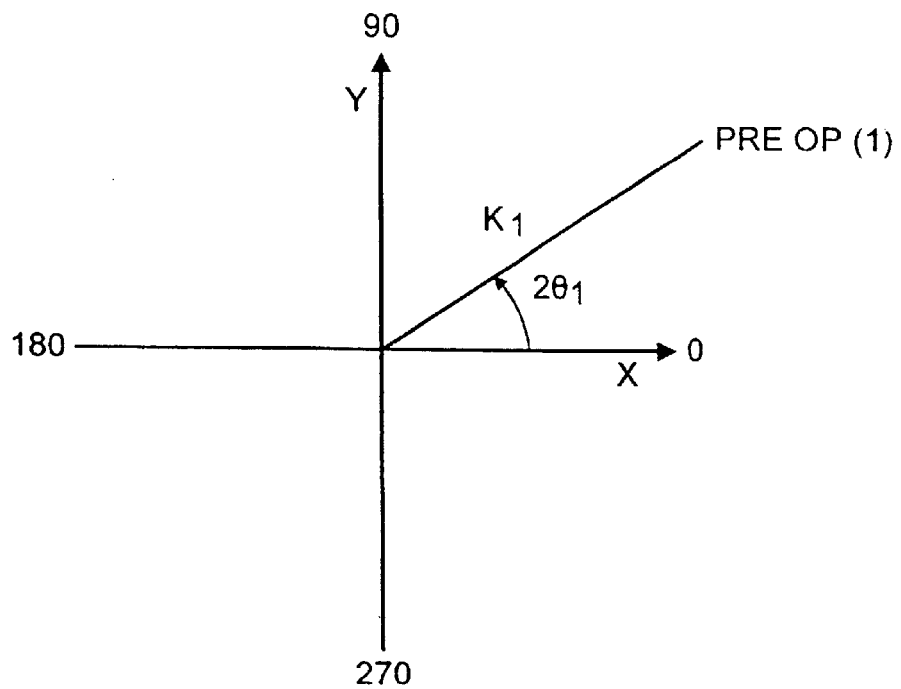
FIGS. 2, 3 and 4 are double angle vector diagrams for the astigmatism values shown in FIG. 1.
Figure 3:
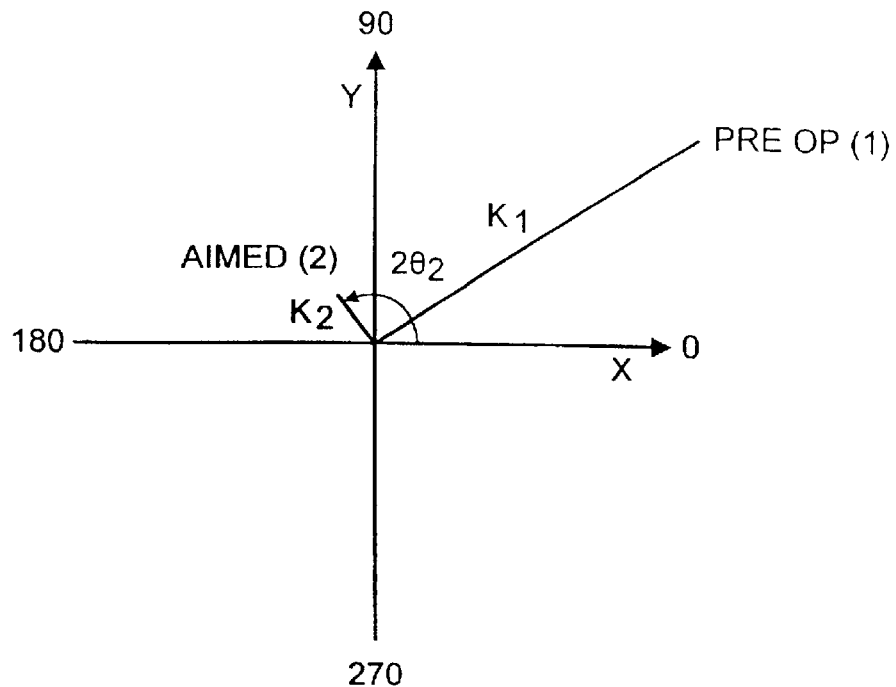
Figure 4:
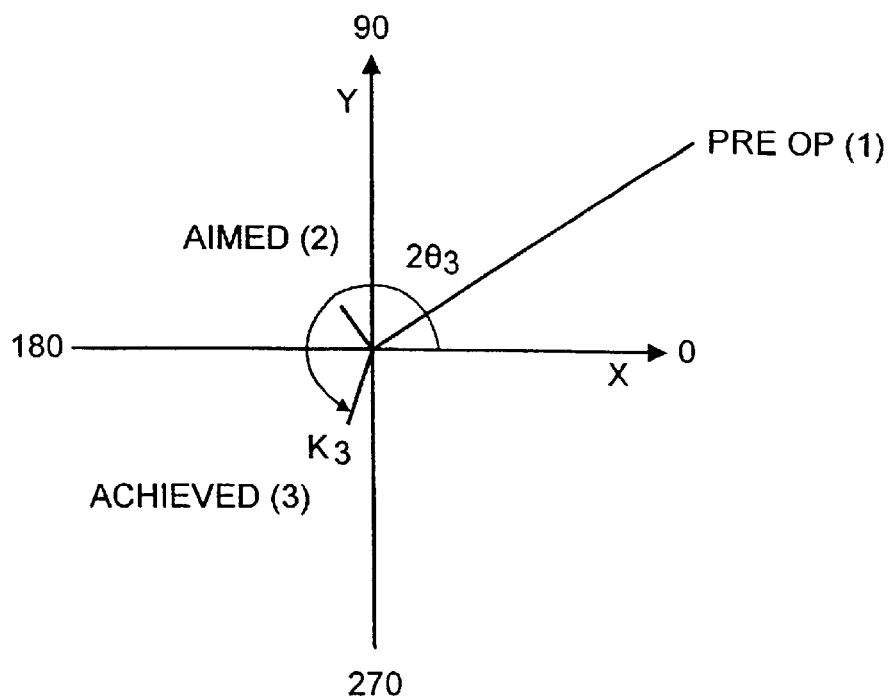

Doubling the angles ensures that results are examined in a 360° sense, so that rectangular co-ordinates may be used. Doubling the angles simplifies interpretation of differences between pre-operative, aimed and achieved astigmatic values, and is necessary in order to determine the magnitude and direction of the surgical vectors. FIGS. 2 to 4 show a diagram in which the angles shown in FIG. 1 have been doubled.

In order to calculate angles and magnitudes, polar co-ordinates are first converted to rectangular co-ordinates as follows:

$X_1 = K_1 \cosine(2\theta_1)$ $Y_1 = K_1 \sine(2\theta_1)$ $X_2=K_2$ cosine $(2\theta_2)$ $Y_2=K_2$ sine $(2\theta_2)$ $X_3=K_3$ cosine $(2\theta_3)$ $Y_3=K_3$ sine $(2\theta_3)$ where: $X_1$, $X_2$ and $X_3$ are the X axis co-ordinates on a 360° vector diagram and $Y_1$, $Y_2$ and $Y_3$ are the Y axis co-ordinates.

Figure 5:
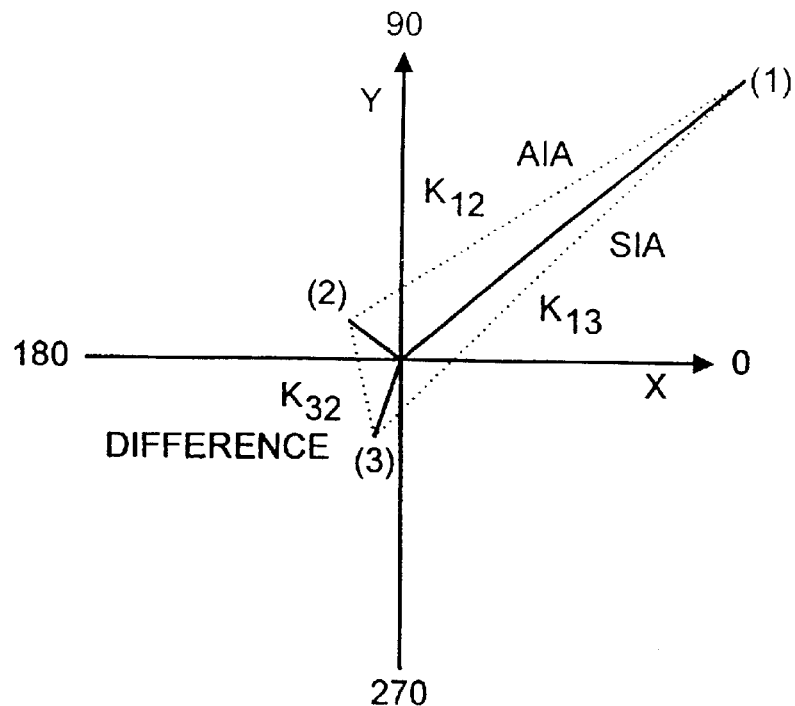
FIG. 5 is a diagram showing double angle vector diagrams and in particular showing an aimed induced astigmatism vector, a surgically induced astigmatism vector and a difference vector.

FIG. 5 shows the Aimed Induced Astigmatism (AIA) vector, the Surgical Induced Astigmatism (SIA) vector and the Difference Vector.

The differences between the X and Y axis co-ordinates of the pre-operative (1), aimed (2) and achieved (3) astigmatisms are therefore:

$X_{12}=X_2-X_1$ $Y_{12}=Y_2-Y_1$ $X_{13}=X_3-X_1$ $Y_{13}=Y_3-Y_1$ $X_{32}=X_2-X_3$ $Y_{32}=Y_2-Y_3$

Double-angle values of the astigmatism vectors are calculated using the X and Y axis differences:

$$\theta_{12d} = \arctan \frac{(Y_{12})}{(X_{12})}$$

$$\theta_{13d} = \arctan \frac{(Y_{13})}{(X_{13})}$$

$$\theta_{32d} = \arctan \frac{(Y_{32})}{(X_{32})}$$

The subscript d refers to double angle.

The arctangent calculation returns a value within the first and fourth quadrants. That is, it does not distinguish whether the angle is in a "to-from" or "from-to" sense. A 180° correction is required when the magnitude (see below) is calculated to be a negative value, as the required angle actually lies in the second and third quadrants.

The magnitude of the astigmatism vectors $K_{12}$ (AIA Aimed Induced Astigmatism), $K_{13}$ (SIA Surgically Induced Astigmatism) and $K_{32}$ (Difference Vector) can now be calculated:

$$K_{12} = \frac{Y_{12}}{\text{sine }(\theta_{12d})}$$

$$K_{13} = \frac{Y_{13}}{\text{sine }(\theta_{13d})}$$

$$K_{32} = \frac{Y_{32}}{\text{sine }(\theta_{32d})}$$

Both positive and negative values for $K_{12}$, $K_{13}$ and $K_{32}$ are possible. Negative values indicate that the values of $\theta_{12d}$, $\theta_{13d}$ and $\theta_{32d}$ need to be adjusted by 180°. Once such corrections to the angles are made, the absolute values of the magnitudes are used.

The above method of calculation differs from the method adopted by Jaffe and Clayman who used the Law of Cosines to determine the magnitude of the SIA as below (conformed for FIG. 5):

$K_{13}=(K_1^2+K_3^2-2K_1K_3 \text{ cosine } 2(\theta_1-\theta_3))^{1/2}$

The problem with using the Law of Cosines is that the sign of the value calculated is not determinable and by convention is taken as being positive (i.e. the square root of the square of −4 is evaluated as +4).

The alternative method of calculation used here to determine $K_{12}$, $K_{13}$ and $K_{32}$ returns the same absolute value as that obtained via the Law of Cosines, but with either a positive or negative sign. A positive value indicates that the value calculated for $\theta_{12d}$, $\theta_{13d}$ or $\theta_{32d}$ does not require adjustment. A negative value means that the required angle is 180° different from that calculated, i.e. it lies in the second and third quadrants.

If the Law of Cosines is used, additional calculations and tests are required to determine when a 180° correction must be made to the double-angle value of $\theta_{12d}$, $\theta_{13d}$ or $\theta_{32d}$.

The calculated values for the vector angles $\theta_{12d}$, $\theta_{13d}$ and $\theta_{32d}$ are derived via the double-angle vector diagram. The actual vector angles are of half the size:

$$\theta_{12} = \frac{\theta_{12d}}{2}$$

$$\theta_{13} = \frac{\theta_{13d}}{2}$$

$$\theta_{32} = \frac{\theta_{32d}}{2}$$

Figure 7:
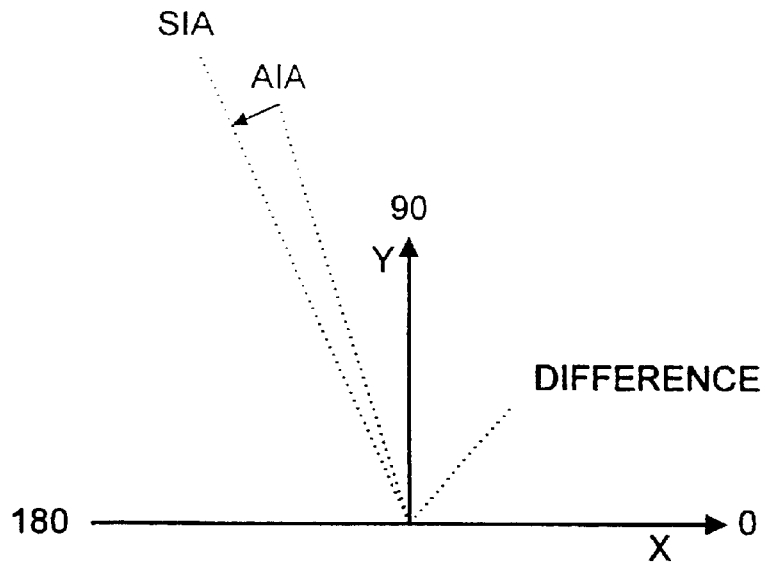
FIG. 7 shows a diagram in which the surgical vectors of FIG. 6 are analysed.

The angle of error is expressed as being positive when the SIA vector lies further anti-clockwise than the AIA vector, and as negative if the change is further clockwise (see FIG. 7). The magnitude of error is expressed as a positive value if the SIA vector is larger than the AIA vector and as negative if smaller than the AIA vector.

The angle of error is most readily calculated from the double-angle values of the AIA vector and the SIA vector (FIG. 5). On the 0° to 180° single-angle vector diagram (FIG. 7), the angle appears as the angle between the vectors. However, if the absolute value of the $\theta_{error}$ is greater than 90 degrees, the angle is adjusted to bring it into the 0 to 90 degree range, by adding the smaller angle to 180° minus the larger angle.

The angle of error is calculated as:

$$\theta_{error} \frac{(\theta_{13d}-\theta_{12d})}{2}$$

The magnitude of the error is calculated as:

$K_{error}=K_{13}-K_{12}$

The difference vector represents the amount of astigmatic correction still to be induced to reach the aimed result from the achieved result; its corresponding orientation of action is from point 3 to point 2 (FIG. 5).

The angle of the difference vector is:

$$\theta_{diff} \frac{\theta_{32}}{2}$$

The magnitude of the difference vector is:

$K_{diff}=K_{32}$

Whereas the angle of error relates to the AIA vector and SIA vector, the angle of correction deals with the aimed and achieved astigmatism. The difference between the aimed and achieved astigmatism angles is defined as the angle of correction.

The angle of correction is:

$$\theta_3 - \theta_2$$

A positive value indicates that the result is anti-clockwise of the aim and a negative value means that it is further clockwise. The value is independent of the pre-operative astigmatism.

Whilst the angle of correction is a measure of the final astigmatic result, it is not as useful as the angle and magnitude of error values in determining and comparing the success of astigmatic surgery.

The Coefficient of Adjustment adapts future astigmatism values to take account of a past trend of variance between the aimed and achieved astigmatism vectors. The coefficient of adjustment is:

$$\frac{K_{12}}{K_{13}}$$

The index of success relates to the magnitude of the differences vector and to the magnitude of the AIA vector.

Index of success:

$$\frac{K_{32}}{K_{12}}$$

The index of success can only be used if an attempt has been made to induce an astigmatic change in the eye.

Unlike astigmatism, vectors cannot be measured; they can only be calculated. Vectors are like surgical navigation aids. They indicate both the direction of future surgery and the success of past surgeries.

The difference vector is specific to the one eye in which it is calculated; however, utilising the magnitude of this vector alone does provide a measure of the success of surgery, and can provide a useful basis for statistical analysis between multiple operations when axis direction is ignored. (This is similar to the current method of averaging SIA (Jaffe method) to determine mean total induced astigmatism for a series of eyes). It specifically represents the magnitude and axis of the difference in diopters between the operative result aimed for and the result achieved. The angle is half that subtended on the vector diagram; by placing its magnitude on a 180° chart, it would describe in a practical sense, the dioptric correction (the amount of steepening and its axis) required for a "top-up" operation to achieve the aimed result for that eye.

The magnitude in diopters gives a measure of the total vector distance between the aimed and the achieved results on the vector diagram.

Magnitude and angle of error are both standardised parameters that are measurable for, and directly comparable between, a series of multiple refractive surgery procedures and can determine the trend of a particular procedure. Mean and standard deviation values can be derived, providing statistical analysis. This method separates the components of the operative error, namely magnitude and axis, and indicates modifications to the original surgical plan required to achieve the aimed result, thereby enabling improved technique for subsequent surgery.

The success of a series of operations can be assessed by determining how close the mean magnitude and axis of error are to zero.

Methods of surgical technique currently employed to make separate alterations to magnitude and axis include:

For magnitude:
 changing the number of T-(tangential) cuts;
 increasing or decreasing the optical zone size;
 changing the length or depth of T-cuts;
 altering the dimensions of the major or minor axes of the elliptical optical zone, or modifying the dimensions and thickness of the ablatable mask in the excimer lasers employing these respective techniques.

For axis:
 changing the steepest axis by 90° by correcting astigmatism in excess of the pre-operative magnitude;
 offsetting T-cuts from the steepest axis.

The potential exists for future excimer laser techniques, utilising the AIA vector, to rotate the ellipse or the ablatable mask by a calculated amount from the steepest meridian of the cornea, to achieve a nominated refractive and astigmatic aim.

a) Magnitude of error:

This is the difference in length or magnitude between the SIA (surgically induced astigmatism) vector and the AIA (aimed induced astigmatism) vector (FIG. 7). An over-correction has occurred if the SIA vector is longer than the AIA vector; an under-correction if it is shorter.

b) Angle of error:

This is half the angle substended on the vector diagram (FIG. 5) by the AIA and SIA vectors at the point (1) of the pre-operative astigmatism value. It can determine, in a series of eyes, for example if there is an error bias occurring towards a consistent axis, which is indicative of technique or machine error. Randomly spread error both positive and negative signs would suggest patient factors are more likely to be at play.

The sign of the angle indicates the direction in which the angle is in error; future corrective surgical action can then be adjusted accordingly.

Figure 6:
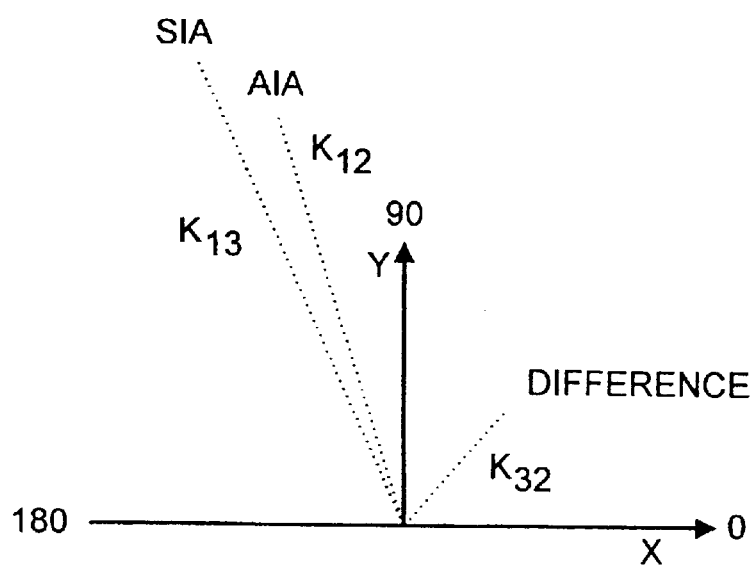
FIG. 6 is a view showing half angle surgical vectors.

The AIA vector and the SIA vector can be represented on a 180° diagram (FIGS. 6 & 7) by halving their respective angles; this determines the angle of error and its orientation. Here, the separation between the two vectors is the angle of error, and the correction of surgical axis direction required is from the induced towards the aimed.

The angle of correction is simply the angle between aimed and achieved astigmatism.

The angle of correction is zero if the aimed and achieved astigmatism axes coincide; the same can be said on the vector diagrams if the axes coincide on the same side of the zero co-ordinates. If the achieved and the aimed astigmatism differ in magnitude but coincide in axis there is a residual difference vector, angle of error and magnitude of error.

However, distinguishing between under and over correction according to the relative proximity of aimed or achieved astigmatism to pre-operative astigmatism would not appear to provide information of practical value.

A coefficient measuring the adjustment required to improve future surgeries can be derived from past surgical data, by dividing the AIA vector by the SIA vector. This coefficient can be averaged for a series of eyes. If it varies significantly from unity, a trend is apparent. If warranted, the magnitude of astigmatism to be corrected in future surgeries can be adjusted accordingly, to take account of the discernible trend. By multiplying the magnitude of the pre-operative astigmatism by the coefficient of adjustment, a magnitude parameter can be obtained, indicating treatment required to obtain the optimal surgical result.

A coefficient value of one indicates that there is no magnitude of error, and that there is no need to make this adjustment to future treatment. A value greater an one indicates that magnitude has been under-corrected; if the value is less than one, over-correction has occurred.

The index of success is a useful measure of the success of the surgery. It is proportional directly to the difference vector and inversely to the AIA vector. The ratio is independent of the size of pre-operative astigmatism. A value of zero on the index of success indicates complete success in achieving the surgical aim; and axiomatically the difference vector magnitude would also be zero. If only one of the angle of error or magnitude or error is zero, the index of success figure will be a number greater than zero. If the index might lie between 0 and one; for example, a value of 0.2 would indicate 80% success has been achieved in attaining the surgical goal. If the index of success is one, then surgery has resulted in achieved astigmatism being equally far away from the aimed as pre-operative astigmatism was. There may or may not have been an astigmatic change; either way, the situation has been made worse because the eye has undergone surgery without improvement in its astigmatic state. The index of success can exceed one, indicating a result worse than the pre-operative state.

The index can only be used if the surgeon has attempted to change the astigmatic state of the eye. For example, in an eye that has a small amount of astigmatism associated with myopia, the surgeon may choose only to induce a spherical correction to correct the refractive error. In such as case, the index of success cannot be used.

Figure 8:
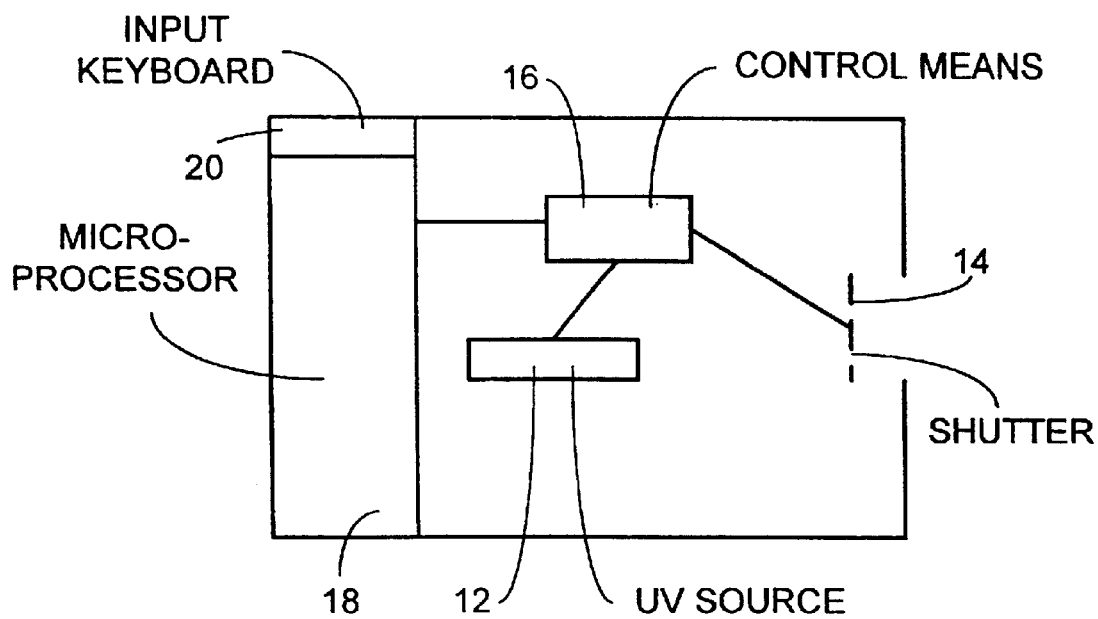
FIG. 8 is a schematic diagram of an apparatus for performing corneal surgery.

With reference to FIG. 8 an apparatus for performing corneal surgery is shown in schematic form. Such apparatus are generally well known and therefore the apparatus is not shown in full detail. The apparatus comprises a source of ultraviolet radiation 12 for producing a beam of ultraviolet radiation (193 nm) which will perform one or more cuts or contouring of a patient's cornea to change the astigmatic state of the patient's eye. A shutter 14 is provided for selectively allowing or shutting off the beam of radiation from the source 12. A control mechanism 16 is provided to control the intensity of the source 12 and also the opening time duration and the speed of opening or closing of the shutter 14 so that a beam of particular intensity for a particular time period can be provided. A microprocessor 18 is coupled to the control mechanism 16 and includes an input keyboard 20 for inputting data into the microprocessor. Data relating to the pre-operative astigmatism of the patient and the aimed astigmatism of the patient is fed into the keyboard 20 and the microprocessor 18 calculates an aimed induced astigmatism vector which is the difference between the aimed astigmatism and the pre-operative astigmatism and used as that vector to produce output commands to the control mechanism 16 for controlling the source 12 and shutter 14.

The microprocessor may also be programmed in accordance with the method hereinbefore disclosed to calculate the other parameters in accordance with the method of this invention for use in analysis and/or further surgery.

The astigmatic module for elliptical treatment patterns recently introduced for the Excimer laser has enabled the corneal shape to be changed in a precise and graduated manner to match the astigmatic refractive error. Current accepted practice is to treat the spectacle refraction adjusted for effectivity at the corneal plane, with secondary regard to the corneal shape. There is frequently a significant variance between spectacle and corneal astigmatism, and this becomes perplexing when one considers that differing readings are obtained with various types of keratometers according to the optical zone measured. The recent introduction of corneal topography technology has made this inconsistency more prevalent. Clearly, to obtain meaningful data, the same type of instrument should be used for all sequential readings: corneal topography, where available, is likely to become the preferred mode.

If the eye is treated using the refraction as the treatment parameter, and there is a variance between corneal and spectacle astigmatism, it is axiomatic that unavoidable non-zero corneal astigmatism will result. With astigmatic keratotomy, it is accepted practice to apply the tangential incisions at the steepest axis, with secondary regard to the refraction: the same unavoidable consequence of non-zero astigmatism is conversely destined for the refraction. After astigmatic keratotomy, it is not an infrequent occurrence to be satisfied with our surgical endeavours, using the keratometry reading as a criteria of success, and yet be disappointed that the patient may complain of symptoms such as monocular diplopia and oblique contours, or may still require astigmatic correction in their spectacles.

The cornea is a convex surface and is steeper in its vertical meridian when with-the-rule astigmatism is present —the axis of the convex cylinder lying at 180°. The clearest retinal image to this eye lies in the vertical meridian. Eggars has shown that this provides an advantage to visual acuity as measured by Snellen's type, as vertical strokes predominate in the English alphabet characters. Testing by a mathematical model confirmed that, for cases of mild myopia, viewing test objects from 0.5–6.0 meters, 0.50D–0.75D of with-the-rule astigmatism is optimal, resulting in the least amount of summated blur. The nasotemporal overlap of ganglion cells which supply both optic tracts are bilaterally cortically represented. They lie on the vertical midline raphe of retinal receptors and neuronal fibres, centred on the fovea, with a width extending greater than one degree of arc. This provides the mechanism to explain a much lower stereoscopic threshold for vertical objects than those orientated in any other meridian. Monocular clues for determining distance are obtained by utilising parallax error between two objects, and this is achieved most frequently with vertical contour clues, such as light poles. In addition, the cyclodisparity range for fusion is greater for vertical than horizontal line segments.

We should state and write down our goals for astigmatism surgery, just as we do for many other tasks, to enable us to assess our success or shortcomings in achieving our initial aims. By stating our astigmatic goal, we are able to determine how the SIA Vector differs from the AIA Vector. Comparative analyses of surgery, utilising this concept of vector analysis is then made possible, because we can determine differences and errors, and thereby ascertain the correction required for future surgeries. The more accurate and predictable the surgery, the narrower will be the spread of the results.

The concept of the AIA Vector is the key to future astigmatism surgery, utilising techniques such as the Excimer laser. As mentioned earlier, the tendency of past and present techniques of astigmatism surgery is to aim to achieve zero astigmatism, by effectively utilising an AIA Vector force equal in magnitude to the pre-operative astigmatism and at 90° to the axis of the astigmatism. The cornea is flattened in the meridian of the astigmatism, with a net steepening in the direction of the AIA Vector.

It is likely that zero astigmatism will continue to be our astigmatic goal, but aiming for zero astigmatism is a self-imposed limitation that may no longer be necessary or reasonable because of the subtleties afforded us by new technology. Any desired post-operative astigmatism may be sought, such as, for example, 0.5D–0.75D with-the-rule. By utilising the AIA Vector calculated, the required surgery can be keyed in to the appropriate software program of the Excimer laser to achieve the intended corneal toroidal shape.

Non-zero astigmatism is an ineluctable consequence of the conflict between a variance of spectacle and corneal astigmatism. A dilemma exists as to whether the corneal shape or the refraction should be the primary determinative factor addressed in any mode of astigmatism surgery. The method addresses how this dilemma can best be resolved by pre-operatively assessing the least unfavourable result for the secondary surface, to which unavoidable astigmatism will be directed. This can be done by analysing what the astigmatism consequence would be for each surface if an AIA Vector were applied to achieve zero astigmatism at the other surface. The surgeon can then select the preferable AIA Vector to be applied (or a suitable compromise between the two calculated), so that the refractive surface(s) destined to receive non-zero astigmatism is (or are) altered in the most optically and physiologically favourable orientation. The surgeon may choose to pre-operatively select the primary treatment that directs the secondary result closest to with-the-rule astigmatism, with the steepest refracting axis closest to the 90° meridian. Without calculating and specifying a non-zero goal(s), we are unable to determine how successful our astigmatism surgery has been.

The ability to calculate the angle of error accurately now exposes the weakest link in our refractive surgery armamentarium—our inability to identify the steepest corneal meridian precisely by real-time topography through the operating microscope during surgery. Achieving this would enable accuracy in applying treatment to approach the. accuracy we possess in measuring and calculating the treatment parameters.

The method described in this paper provides the astigmatism surgeon with additional information not previously available, enabling a mathematically precise evaluation of surgery, using parameters which will allow comparison both between different eyes and different techniques. These parameters also enable the surgeon to ascertain the means of attaining any desired level of post-operative astigmatism. It is only by meaningfully and critically analysing our astigmatism surgery that we will be able to improve it. Now that we can determine specific errors, we are provided with the means of correcting each component of our error separately. By being able to make better use of current technologies we will achieve better control and ultimately, more accurate surgery.

I claim:

1. An article encoded with a computer readable program for operating a computer to obtain parameters related to a surgical procedure to correct astigmatism in the eye of a patient, said program being provided with magnitude and angle values of measured pre-operative astigmatism of an eye of a patient and magnitude and angle values of a non-zero aimed astigmatism to be achieved following surgery on the eye of the patient, said program being operative to determine parameters related to said pre-operative measured values of magnitude and angle to provide parameters concerning treatment of the cornea of the eye of the patient to correct astigmatism said program including;

a routine for vectorially adding the pre-operative astigmatism and the non-zero aimed astigmatism to obtain an aimed induced astigmatism vector to obtain an aimed induced astigmatism vector representing dioptric force and axis intended to achieve said non-zero aimed astigmatism;

said dioptric force and axis of said aimed induced astigmatism vector representing parameters for surgery on the eye to effect relative steepening of the cornea in a direction and magnitude corresponding to the aimed induced astigmatism vector.

2. An article with the program as claimed in claim 1, wherein the program can operate a control means of an apparatus to perform corneal surgery based on said parameters produced by said program.

3. An article with the program as claimed in claim 1, wherein the angle values of the measured pre-operative astigmatism and of the aimed astigmatism are measured on respective axes in a 0°–180° range, said program operating to effect;

doubling the angles of the axes of the pre-operative astigmatism and the aimed astigmatism to convert the axes to a 0°–360° range;

calculating said aimed induced astigmatism vector, in said 0°–360° range; and halving the angle of said aimed induced astigmatism vector to return the angle values to the 0° to 180° range.

4. An article with the program of claim 3, wherein said halving of the vector angles includes converting from rectangular coordinates to polar coordinates.

5. An article encoded with a computer readable program for operating a computer to obtain parameters related to a surgical procedure to correct astigmatism in the eye of a patient, said program being provided with magnitude and angle values of measured pre-operative astigmatism of an eye of a patient, magnitude and angle values of aimed astigmatism to be achieved following surgery on the eye of the patient, and post-operative values of magnitude and angle of surgically induced astigmatism after a prior surgery intended to correct said pre-operative astigmatism, said program being operative to determine parameters related to said pre-operative and said post-operative measured values of magnitude and angle to provide parameters concerning treatment of the cornea of the eye of the patient to correct astigmatism said program including;

a routine for vectorially adding the pre-operative astigmatism and the aimed astigmatism to obtain an aimed induced astigmatism vector;

vectorially adding the pre-operative astigmatism and said surgically induced astigmatism to obtain a surgically induced astigmatism vector, and relating said surgically induced astigmatism vector and said aimed induced astigmatism vector to one another and to said values of the components which compose said vectors, to obtain parameters which are indicative of said prior surgery or of still a further surgery to achieve said aimed astigmatism.

6. An article with the program as claimed in claim 5, wherein the program can operate a control means of an apparatus to perform corneal surgery based on said parameters produced by said program.

7. An article with the program as claimed in claim 5, wherein the angle values of the measured pre-operative astigmatism and of the aimed astigmatism are measured on respective axes in a 0°–180° range, said angle of said post-operative astigmatism also being measured on an axis in said 0°–180° range, said program operating to effect;

doubling the angles of the axes of the pre-operative astigmatism, the aimed astigmatism and the post-operative astigmatism to convert the axes to a 0°–360° range;

calculating said aimed induced astigmatism vector, and said surgically induced astigmatism vector in said 0°–360° range; and halving the angle of said aimed induced astigmatism vector and said surgically induced astigmatism vector to return the angle values to a 0° to 180° range.

8. An article with the program of claim 7, wherein said halving of the vector angles includes converting from rectangular coordinates to polar coordinates.

9. An article with the program of claim 5, which determines a coefficient of adjustment by dividing the aimed induced astigmatism vector by the surgically induced astigmatism vector.

10. An article with the program of claim 5, wherein the relating of said vectors and its components comprises calculating a difference vector as the vector difference between the aimed induced astigmatism vector and the surgically induced astigmatism vector and calculating an index of success which is the magnitude of the difference vector divided by the magnitude of the aimed induced astigmatism vector.

11. An article with the program of claim 5, which determines an angle of correction which is the angular difference between the aimed astigmatism and the post-operative astigmatism.

12. An article with the program of claim 5, which determines a magnitude of error as the magnitude difference between the surgically induced astigmatism vector and the aimed induced astigmatism vector.

13. An article with the program of claim 5, which calculates an angle of error which is the angular difference between the surgically induced astigmatism vector and the aimed induced astigmatism vector.

14. An article with the program of claim 5, which determines what the non-zero astigmatism consequences would be for one of the corneal surface and a spectacle surface if the aimed induced astigmatism vector were applied to achieve zero astigmatism at the other one of the corneal and spectacle surfaces.

15. A method of obtaining parameters related to surgery on the cornea of an eye of a patient to correct astigmatism of the eye, said method comprising the steps of:

examining an eye of a patient for astigmatism and evaluating the astigmatism in terms of magnitude at an angle of steepest axis;

defining magnitude and angle values of a non-zero aimed astigmatism to remain following surgery;

vectorially adding the evaluated pre-operative astigmatism and the non-zero aimed astigmatism to obtain an aimed induced astigmatism vector representing dioptric force and axis intended to achieve said non-zero aimed astigmatism;

said dioptric force and axis of said aimed induced astigmatism vector representing parameters for surgery on the eye to effect relative steepening of the cornea in a direction and magnitude corresponding to the aimed induced astigmatism vector;

measuring magnitude and angle values of post-operative astigmatism values following surgery on the eye of the patient, vectorially adding the post-surgical values of astigmatism following the surgery and the values of astigmatism prior to the surgery to obtain a surgically induced astigmatism vector, and relating said surgically induced astigmatism vector and said aimed induced astigmatism vector to one another and to the values of the components which compose said vectors to obtain parameters which characterize said prior surgery or are applicable to carry out further surgery to achieve said aimed astigmatism.

16. The method of claim 15 wherein the step of evaluating pre-operative astigmatism comprises making corneal measurements of the eye of the patient or utilizing information relating to of refractive correction of the eye of the patient.

17. The method of claim 15, wherein the relating of said surgically induced astigmatism vector and said aimed astigmatism vector comprises determining a coefficient of adjustment by dividing the aimed induced astigmatism vector by the surgically induced astigmatism vector.

18. The method of claim 15, wherein the relating of said surgically induced astigmatism vector and said aimed induced astigmatism vector comprises calculating a difference vector as the vector difference between the aimed induced astigmatism vector and the surgically induced astigmatism vector and determining an index of success which is the magnitude of the difference vector divided by the magnitude of the aimed induced astigmatism vector.

19. The method of claim 15 wherein the step of relating the vectors and the values of the components thereof vectorially adding post-operative values and comprises determining an angle of correction which is the angular difference between the aimed astigmatism and the post-operative astigmatism.

20. The method of claim 15, wherein the step of relating the vectors and the values of the components thereof comprises determining a magnitude of error which is the magnitude difference between the surgically induced astigmatism vector and the aimed induced astigmatism vector.

21. The method of claim 15 wherein wherein the step of relating the vectors and the values of the components thereof comprises calculating an angle of error which is the angular difference between the surgically induced astigmatism vector and the aimed induced astigmatism vector.

22. The method of claim 15, wherein the angle of the steepest axis measured during said examining is in a range of 0° to 180° and said aimed astigmatism is represented with a magnitude at an angle also in a range of 0° to 180°, said method further comprising doubling the angles of the measured pre-operative astigmatism, the post-operative astigmatism and the aimed astigmatism to convert the angles to a 0° to 360° range, obtaining said aimed induced astigmatism vector and said surgically induced astigmatism vector in said 0° to 360° range, and dividing the angles of the aimed induced astigmatism vector and the surgically induced astigmatism vector by 2 to bring said angles to the 0° to 180° range.

23. The method of claim 22, wherein the step of dividing the vector angles includes the step of converting from rectangular coordinates to polar coordinates.

24. The method of claim 15, wherein the relation of the vectors and the components comprises calculating magnitude and angle values of a difference vector which is the vector difference between the aimed induced astigmatism vector and the surgically induced astigmatism vector.

25. The method of claim 15, wherein the relating of said surgically induced astigmatism vector and said aimed astigmatism vector comprises dividing the magnitude of one of the surgically induced astigmatism vector and the aimed induced astigmatism vector by the other.

26. A method of obtaining parameters related to surgery on the cornea of an eye of a patient to correct astigmatism of the eye, said method comprising the steps of:

examining an eye of a patient for astigmatism and evaluating the astigmatism in terms of magnitude at an angle of steepest axis;

defining magnitude and angle values of a non-zero aimed astigmatism to remain following surgery; and vectorially adding the evaluated pre-operative astigmatism and the non-zero aimed astigmatism to obtain an aimed induced astigmatism vector representing dioptric force and axis intended to achieve said non-zero aimed astigmatism;

said dioptric force and axis of said aimed induced astigmatism vector representing parameters for surgery on the eye to effect relative steepening of the cornea in a direction and magnitude corresponding to the aimed induced astigmatism vector.

27. The method of claim 26, wherein the angle of the steepest axis measured during said examining is in a range of 0° to 180° and said aimed astigmatism is represented with a magnitude at an angle also in a range of 0° to 180°, said method further comprising doubling the angles of the measured pre-operative astigmatism and of the aimed astigmatism to convert the angles to a 0° to 360° range, obtaining said aimed induced astigmatism vector in said 0° to 360° range, and dividing the angles of the aimed induced astigmatism vector by 2 to bring said angles to the 0° to 180° range.

28. The method of claim 27, wherein the step of dividing the vector angles includes the step of converting from rectangular coordinates to polar coordinates.

* * * * *